(12) United States Patent  (10) Patent No.: US 7,414,395 B2
Gao et al.  (45) Date of Patent: Aug. 19, 2008

(54) METHOD AND APPARATUS INSPECTING PIPELINES USING MAGNETIC FLUX SENSORS

(75) Inventors: Ming Gao, Houston, TX (US); Sergio Limon, Bountiful, UT (US); Richard Clark McNealy, Houston, TX (US); Ron Sherstan, Cypress, TX (US)

(73) Assignee: General Electric Company, Schenectady, NY (US)

( * ) Notice: Subject to any disclaimer, the term of this patent is extended or adjusted under 35 U.S.C. 154(b) by 12 days.

(21) Appl. No.: 11/277,523

(22) Filed: Mar. 27, 2006

(65) Prior Publication Data

US 2007/0222436 A1   Sep. 27, 2007

(51) Int. Cl.
*G01N 27/72* (2006.01)
(52) U.S. Cl. .................. 324/220; 324/228; 324/238
(58) Field of Classification Search ................ 324/220, 324/240, 221, 238, 239, 242, 243, 228; 73/622, 73/623, 643; 702/34, 35, 38
See application file for complete search history.

(56) References Cited

U.S. PATENT DOCUMENTS

| 6,127,823 | A  | * | 10/2000 | Atherton ................. 324/220 |
| 7,002,340 | B2 | * | 2/2006  | Atherton ................. 324/220 |
| 2001/0017541 | A1 |   | 8/2001  | Kwun et al. |
| 2001/0029989 | A1 |   | 10/2001 | Paz |
| 2003/0198374 | A1 |   | 10/2003 | Hagene et al. |
| 2004/0183528 | A1 |   | 9/2004  | Crouch et al. |
| 2004/0211272 | A1 |   | 10/2004 | Aronstam et al. |
| 2004/0217759 | A1 |   | 11/2004 | Burkhardt et al. |

OTHER PUBLICATIONS

P.A. McVeigh et al., "Analysis of Surface Stresses And Stress Intensity Factors Present During Fretting Fatigue", American Institute of Aeronautics and Astronautics, 1999, pp. 1188-1196.

(Continued)

*Primary Examiner*—Reena Aurora
(74) *Attorney, Agent, or Firm*—Nixon & Vanderhye P.C.

(57) ABSTRACT

The method for detecting stress corrosion cracking (SCC) of pipelines, comprising the steps of: identifying pipeline locations and pipeline conditions that are amenable to inspection by a magnetic flux inline tool and by a TFI tool; performing two inspections on the pipeline, one inspection performed using the magnetic flux inline (MFL) tool and an other inspection performed using the TFI tool; aligning signal features resulting from the two inspections; identifying TFI signals occurring above a specified threshold; identifying MFL signals for a section of pipeline corresponding to the identified TFI signals; for the identified TFI signals, determining whether the MFL signals are below a second threshold level; designating the sections of the pipeline corresponding to identified TFI signals above the threshold and below the second threshold as a potential corrosion feature; identifying TFI signals that exceed a defined metal loss percentage; measuring a width and length of the signal features, and if the width and length of the signal feature exceed threshold crack width and length values, designating as a potential corrosion feature section of pipeline corresponding to the identified TFI signals.

20 Claims, 8 Drawing Sheets

OTHER PUBLICATIONS

Yang-Lijian et al., "Research on Intelligent Pipeline Magnetic Flux Leakage Detector", 10th Asia-Pacific Conference on Non-Destructive Testing, (Sep. 17-21, 2001), pp. 1-4.

Dr. Pierre-Olivier Bouchard, "3D Numerical Modelling of Damage and Fracture—Towards An Integrated Approach Between Forming Processes and Structural Analysis", Apr. 27-29, 2005, pp. 1-7.

C.D. Lykins et al., "A Shear Stress-Based Parameter For Fretting Fatigue Crack Initiation", 2001 Blackwell Science Ltd. Fatigue Fract Engng Mater Struct 24, 461-473, (2001).

Ron Sherstan et al., "Using Cost Effective MFL Inspections As An SCC Screening Tool", email from Shahani Kariya Wasam Mar. 24, 2006, Apr. 2005 (Spring 2005 NACE), pp.1-14.

* cited by examiner

| DIG # | US WELD # | ANOMALY DISTANCE FROM GW | DIST FROM GW | ORIENTATION | ORIGINAL PREDICTION | NEW PROCESS PREDICTION | ANOMALY FOUND |
|---|---|---|---|---|---|---|---|
| 1 | 14920 | 57043.2 | 13.3 | 9:15 | Medium Probability | low probability, small signal in MFL | shallow mill grinds |
| 2 | 14960 | 57210.5 | 20.3 | 4:30 | Medium Probability | low probability, signal appears to be in long seam | shallow mill grinds |
| 3 | 25700 | 98216.8 | 1.3 | 11:15 | Medium Probability | low probability, signal appears to be in long seam | mill scale / other non-associated minor SCC 10 - 15% |
| 4 | 32660 | 125134.9 | 11.1 | 4:00 | High Probability | high probability | SCC - 47% |
| 5 | 34360 | 131605.4 | 27.9 | 7:00 | Medium Probability | high probability | SCC - 28% |
| 6 | 42170 | 161219.8 | 28.7 | 5:00 | Medium Probability | very low probability, very small TFI signal | linear indication / minor SCC corrosion site, alignment error in data |
| 7 | 60070 | 230820.4 | 26 | 8:15 | Medium Probability | NO, large signals on MFL | caused miscall |

Fig. 10

METHOD AND APPARATUS INSPECTING PIPELINES USING MAGNETIC FLUX SENSORS

BACKGROUND OF THE INVENTION

This invention relates to inspecting pipelines for cracks and, in particular, to inspecting pipelines using magnetic flux leakage inspection principles.

The increasing occurrence of stress corrosion cracking (SCC), especially in North America, and increased regulatory requirements creates a need for pipeline operators to identify pipelines with occurring SCC and identify the extent and severity of SCC. There is a justifiable reluctance to utilize sophisticated and costly inspection technologies on pipelines where little or no SCC has be identified thru normal maintenance operations (cut outs, corrosion investigations and others). On some pipeline sizes there is no available technology to survey the pipelines using the sophisticated technologies, due to size restrictions, tight bends, product type or speed, and other considerations.

SCC is typically found on pipelines, such as high pH (e.g., pH 9-13) SCC (also referred to as 'classical SCC') generally appears as intergranular cracking whereby a thick oxide layer forms on the pipe in a heavily concentrated carbonate-bicarbonate soil environment. Load variances on a pipe can cause crack tip strain that results in destruction of the oxide layer and further extension of the crack. A newer form of SCC, near-neutral pH (e.g., 5-7) SCC (also referred to as non-classical SCC), appears as transgranular cracking and is usually caused by groundwater containing $CO_2$ which originates from sources such as disbonded pipeline coatings. Resulting cracks may be further aggravated by cyclical loads associated with the pipelines due to the stress ratios placed on these loads. Other elements present in the environment, such as hydrogen, have also been found to contribute to the susceptibility of SCC.

Pipeline operators and owners maintain integrity management plans (IMPs) for addressing procedures for maintaining pipelines. The procedures provide processes and recommended tools for performing routine maintenance, assessments, and corrective activities for ensuring the continued operation of the pipeline, as well as for ensuring environmental and public safety relating to these operations. Existing pipeline inspection procedures can be expensive, invasive, and laborious. For example, determining SCC by physical inspection often requires extensive excavation of a pipe and manual examination by the human eye. Further, many existing tools and processes for pipe inspection address or uncover one or more specific types of pipe defects or are geared toward a specific type of pipeline, and are not equipped to handle the variety of known issues, defects, and pipeline types that are in operation today. It is desirable to provide a way to manage pipeline conditions that covers a variety of operational conditions without incurring undue expense and labor.

SUMMARY OF THE INVENTION

A system and method has been developed to identify cracks in pipelines using magnetic flux leakage inspection principles and flux data obtained by passing an inline inspection vehicle through a pipeline. The inline inspection vehicle includes onboard sensors generate flux data regarding magnetic flux lines (MFL) and transverse magnetization flux lines (TFI) on the pipe. The MFL magnetic field is an axially oriented magnetic field and the TFI field is a circumferentially oriented magnetic field.

The flux data is analyzed to detect stress corrosion cracking (SCC) in the pipeline. The system may include a collection of procedures and algorithms that include a pre-assessment to determine whether the pressure in a pipeline is sufficient to open stress corrosion cracks sufficiently that they may be reliably detected by analyzing MFL and TFI magnetic flux data. The system and method embody a novel combination of MFL and TFI data analyses technologies. The system presents side-by-side visual displays of signals from the MFL and TFI data of the same region of a pipeline so that the signals can be compared to determine whether cracks are indicated by the MFL and TFI data. The system and method locate critical SCC colonies with a high degree of confidence and thereby identify pipe sections that should be more directly inspected.

Exemplary embodiments relate to methods, systems and computer program products for detecting stress corrosion cracking (SCC) of pipelines and other metal structures prone to SCC. The method includes identifying pipeline locations and pipeline conditions that are amenable to inspection by conventional a magnetic flux sensors incorporated in inline inspection vehicles.

The method may include identifying pipeline locations and pipeline conditions that are amenable to inspection by a magnetic flux inline sensor tool and by a TranScan TFI sensor tool sold by the General Electric Company. The method may also include performing two inspections on the pipeline, one inspection performed using the magnetic flux inline tool and another inspection performed using the TranScan TFI tool.

The method further includes aligning signal features resulting from the MFL and TFI inspections, and evaluating the aligned signal features for SCC. The method includes determining a number of MFL and TFI signal features that are indicative of potential crack field (PCF) features and potential corrosion features.

The method may also include excavating and inspecting pipe locations associated with the identified crack field or corrosion or excavating and inspecting a selected number of locations associated with the features. Using as feedback information the data obtained regarding the presence of cracks or lack of cracks in the excavated pipes, the algorithms used to analyze the MFL and TFI signal features may be adjusted to better predict the presence of cracks in the pipeline.

The method may detect stress corrosion cracking (SCC) of pipelines, comprising the steps of: identifying pipeline locations and pipeline conditions that are amenable to inspection by a magnetic flux inline tool and by a TFI tool; performing two inspections on the pipeline, one inspection performed using the magnetic flux inline (MFL) tool and an other inspection performed using the TFI tool; aligning signal features resulting from the two inspections; evaluating a number of features detected by the two inspections, the features including potential crack field features and potential corrosion features, and based upon results of the evaluation identifying potential crack fields for physical inspection. Wherein the potential crack field features are determined by a process comprising: identifying TFI signals occurring above a specified threshold; identifying MFL signals for a section of pipeline corresponding to the identified TFI signals; for the identified TFI signals, determining whether the MFL signals are below a second threshold level; designating the sections of the pipeline corresponding to identified TFI signals above the threshold and below the second threshold as a potential corrosion feature.

The method may be embodied as detecting stress corrosion cracking (SCC) of pipelines, comprising the steps of: identifying pipeline locations and pipeline conditions that are amenable to inspection by a magnetic flux inline tool and by a TFI tool; performing two inspections on the pipeline, one inspection performed using the magnetic flux inline (MFL) tool and an other inspection performed using the TFI tool; aligning signal features resulting from the two inspections; identifying TFI signals occurring above a specified threshold; identifying MFL signals for a section of pipeline corresponding to the identified TFI signals; for the identified TFI signals, determining whether the MFL signals are below a second threshold level; designating the sections of the pipeline corresponding to identified TFI signals above the threshold and below the second threshold as a potential corrosion feature; identifying TFI signals that exceed a defined signal amplitude; measuring a width and length of the signal features, and if the width and length of the signal feature exceed threshold crack width and length values, designating as a potential corrosion feature section of pipeline corresponding to the identified TFI signals.

A computer program product has been developed for detecting stress corrosion cracking (SCC) of pipelines, the computer program product including instructions for performing: identifying pipeline locations and pipeline conditions that are amenable to inspection by a magnetic flux inline tool and by a TFI tool; performing two inspections on the pipeline, one inspection performed using the magnetic flux inline tool and an other inspection performed using the TFI tool; aligning signal features resulting from the two inspections; evaluating results of the aligning, comprising: determining a number of features detected by the two inspections, the features including potential crack field features and potential corrosion features; and based upon results of the evaluating, performing at least one of: excavating and inspecting all locations associated with the features; and excavating and inspecting a selected number of locations associated with the features.

DESCRIPTION OF THE DRAWINGS

Exemplary systems and methods illustrating the present invention(s) are described herein below with reference to various figures, in which:

FIG. 10 is a chart of crack data obtained from inspection of pipes that were the subject of excavations.

DETAILED DESCRIPTION OF THE INVENTION

Figure 1:
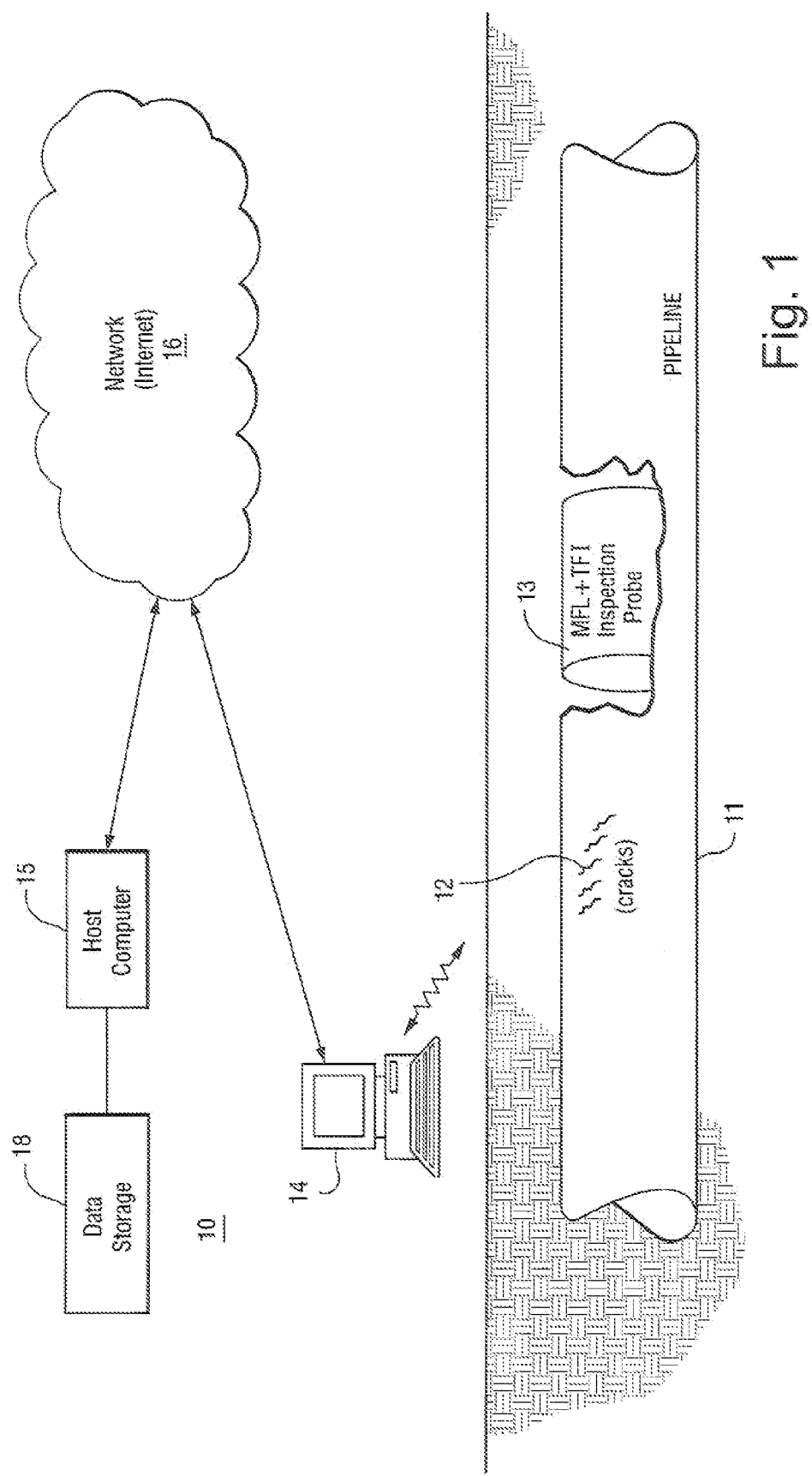
FIG. 1 is a block diagram of a pipeline system and a pipeline inspection and management system.

FIG. 1 shows schematically a system upon which the pipeline inspection and management system 10 may be implemented in the exemplary embodiments described herein. Pipelines may be liquid or gas pipelines. An underground pipeline 11 may have corrosion induced stress cracks 12 that are periodically inspected with a magnetic field probe 13. The probe is used to simultaneously acquire MFL and TFI magnetic flux signal data. Alternatively, a MFL sensor probe and a separate TFI sensor probe may be used and passed separately through the pipe to acquire serially MFL and TFI sensor data. The pipeline management system 10 may include a network of one or more user computers 14, e.g., personal or laptop computers, through which users at one or more geographic locations collect data and may contact a host computer system 15. The host computer system 15 executes computer instructions for managing pipeline data and the user systems 14 are coupled to the host system via a communications network 16. Alternatively, the pipeline management system may be run on a single computer, such as a personal computer or laptop computer 14.

The pipeline management system 10 provides a non-invasive inspection solution for screening pipelines for SCC. The pipeline management system 10 functions may be applied to detect both classic SCC and non-classical SCC. The pipeline management system assesses the factors of stress intensification at crack tips using fracture mechanics and the effects on flux leakage caused by SCC. The pipeline management system performs collects MFL and TFI flux data from one or more pipeline inspections, aligns and evaluates the inspection results, and develops an action plan for the pipeline that includes reinspections, direct examinations, hydrostatic or CD slug testing, and other pipeline inspection activities. The results of the analysis may be used to determine the risk of SCC in the pipeline.

The host computer and/or user system includes a data storage device 18 having data relating to pipelines and integrity management information, e.g., integrity management system plan(s) (IMPs) including re-inspection plans. Also stored in storage device 18 may be crack susceptibility data for various types of pipes used in implementing the pre-assessment process described herein. Stored in storage device 18 may also be inspection history data including corrosion linearity lists/charts and potential crack feature lists, discovery prioritization lists, and pipeline management application reports (e.g., post-inspection data analysis reports). Inspection history files include results of past inspections performed on a pipeline such as signal graphs and signal analyses. Information stored in the storage device 18 may be retrieved and manipulated via the host computer system 15 and/or via the user computer system 14. The host system 15 may operate as a database server and coordinate access to application data including data stored on the storage device 18.

Figure 2:
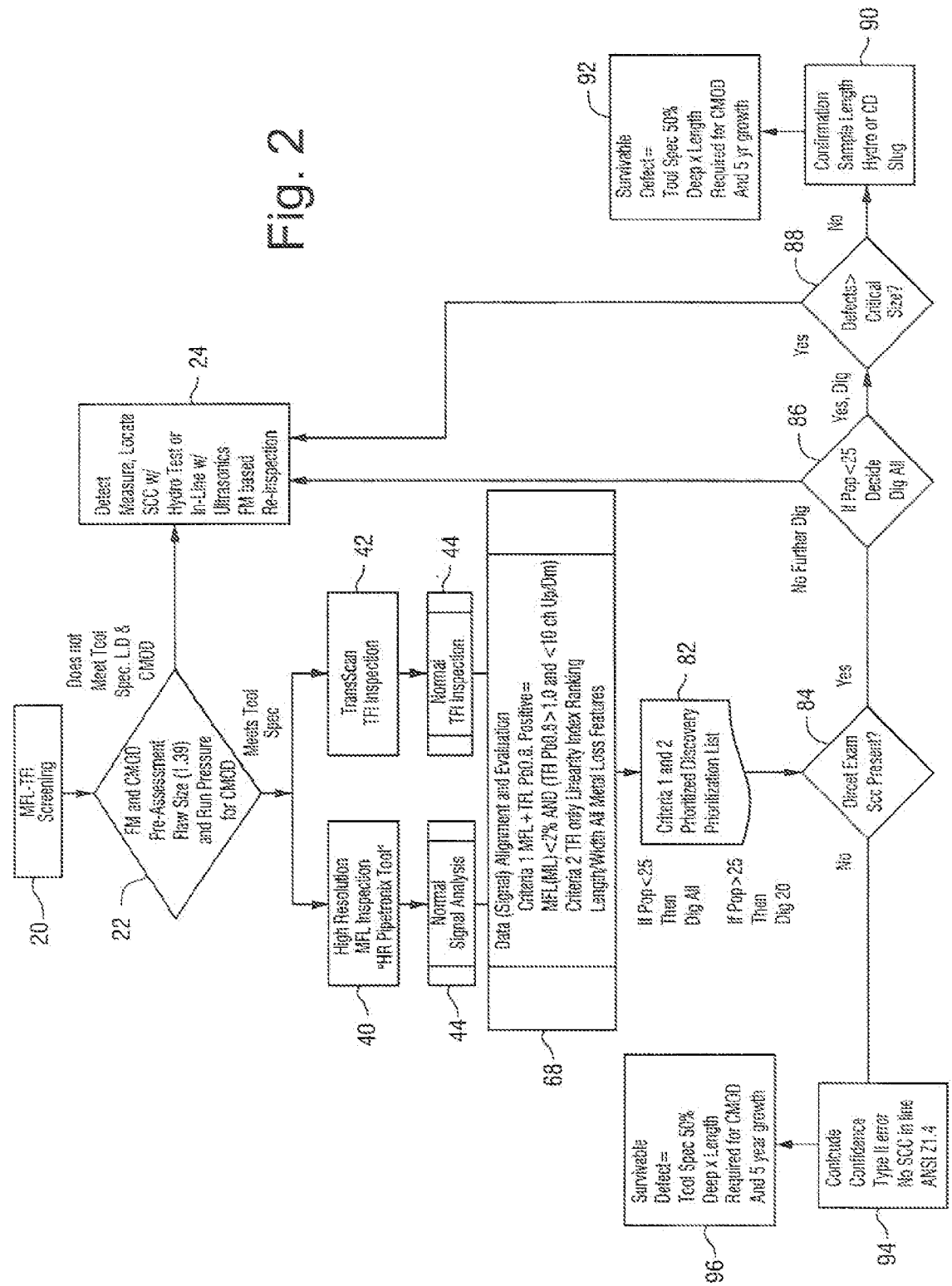
FIG. 2 is a block diagram of a process for implementing the pipeline inspection and management system activities.

FIG. 2 is a flow chart of a MFL-TFI screening process 20. The screening process evaluates magnetic flux data to detect classic and non-classic SCC cracking. Magnetic flux sensors detect changes in magnetic flux induced in a metallic pipe. Flux is relatively uniform along uniform and defect free sections of the pipe. As the flux flows across a crack, there is a corresponding change, e.g., disruption, in the flux. The change is detected by magnetic flux sensors.

There is a concern that narrow cracks do not cause a flux disruption that is sufficient to yield a detectable flux change signal. It is believed that significant flux disruptions occur when flux flows across relatively wide cracks. Narrow cracks disrupt flux to a lesser extent and may not be reliably detected by magnetic sensors.

To ensure that there is a likelihood that cracks are sufficiently wide to be detected, a pre-assessment 22 is made to determine whether the pipe pressure is sufficient for MFL-TFI inspection. It has been determined that cracks become wider as the pressure in a pipe increases. Pipes have some elasticity and deform under pressure. As pipes expand under pressure, cracks in the pipe become wider. If the pressure in a pipe is sufficiently great, SCC cracks become be sufficiently wide to be detected by analyzing MFL-TFI flux data. The pre-assessment step 22 determines whether the pressure in a pipe is great enough for MFL-TFI data signal analysis. At a certain pressure, it can be assumed that the cracks in a pipe are sufficiently wide to be reliably detected by analyzing MFL-TFI data. If the pressure in the pipe is too low, it is deemed that MFL-TFI data analysis is not likely to detect cracks. Alternative methods 24 for detecting cracks are then considered, such as conventional hydro-testing or a combination of in-line ultrasonic testing.

The pre-assessment process 22 may also include gathering historical data such as results of previous inspections (existing defects and their size, extent, number, critical size, etc.), operating conditions (e.g., cyclical loads and pressure, pipeline utility such as whether it is used for liquid or gas products), pipeline specifications, (e.g., pipeline coating materials, pipeline age, pipeline location and soil conditions, pipeline measurements (wall thickness, diameter, length, etc.), and inspection tool capabilities.

For the MFL-TFI inspection to reliably identify SCC, the cracks must have a minimum size. The required minimum flaw size for a defect, e.g., crack width, may be predicted based on a plastic collapse theory for bulk pipe wall defects or brittle fracture theory (Fracture Mechanics) in the case of defects offering stress concentration such as cracks. The capability of MFL and TFI analyses may be a factor in a determination of the suitability of a specific sensor for a given inspection considering the historical data, operating conditions, and pipeline specifications. For example, MFL flux data indicates changes in magnetic stray flux and are used to detect the beginning and end of a long and shallow defect. If flux data is used to MFL data is less helpful in determining the correct depth of the defect. TFI flux data is used to detect transverse magnetization and are useful in detecting wall thickness of longitudinal channeling corrosion over the entire length of a defect. TFI flux data is further useful in detecting narrow crack channels and longitudinal cracks that are open to the surface of a pipeline.

Figure 3:
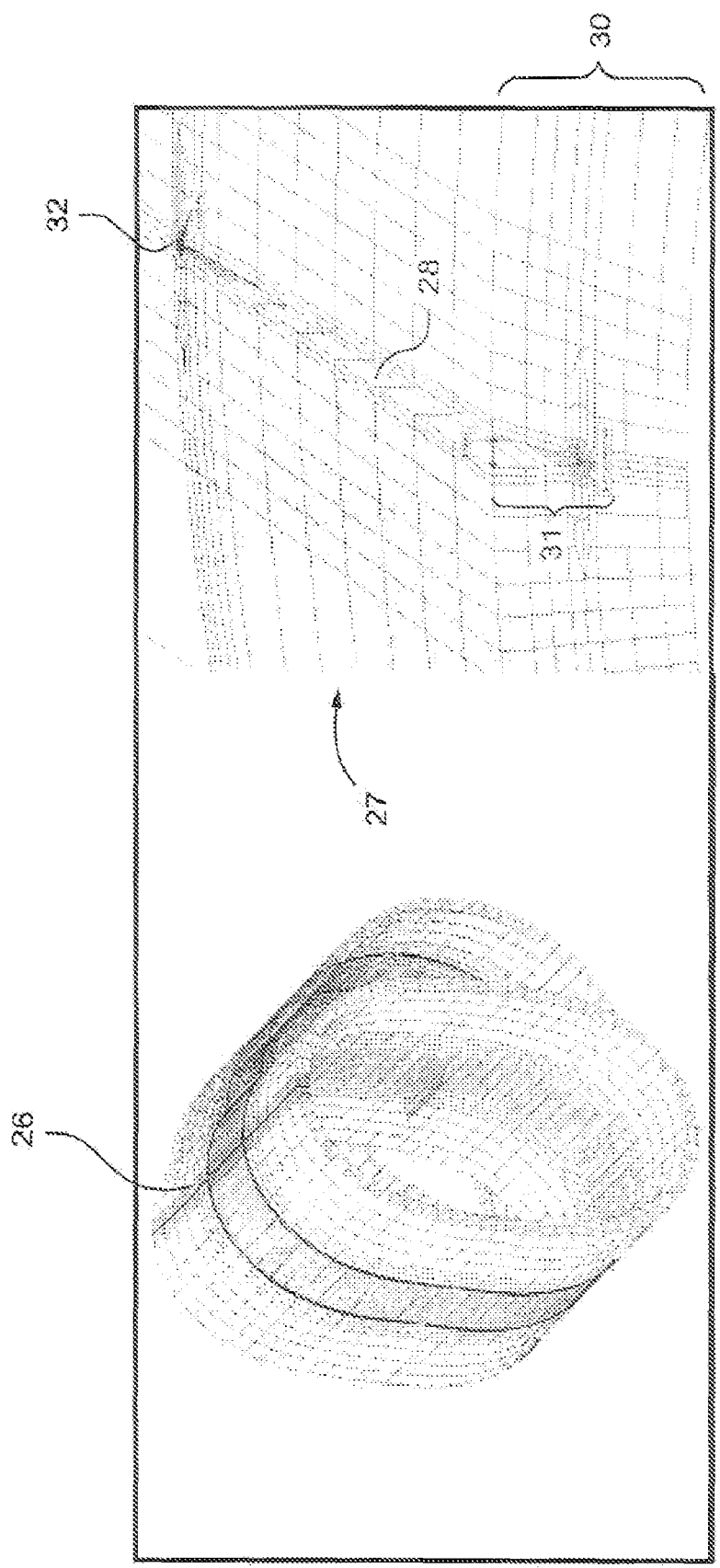
FIG. 3 are schematic diagrams of a finite element mesh representing a section of a pipe having a crack.

To conduct the preassessment 22, an analysis is performed to determine whether the pressure in the pipe is sufficient to open cracks such that can be reliably detected. The graphical charts in FIGS. 3 and 4 further illustrate the pre-assessment process and a means for determining whether pipe pressure is sufficient for MFL and TFI flux data analyses. FIG. 3 is a schematic diagram of a finite element mesh 26 representing a section of a pipe having a crack. An enlarged view 27 of a pipe mesh section shows a crack 28. FIG. 3 illustrates the application of a finite element analysis to develop a series of curves 34 (FIG. 4) used during the preassessment 22 to determine the pressure needed in a pipe to have the critical flaw size (crack mouth opening displacement—CMOD) for the MFL-TFI flux data screening. The mesh representation 26, 27 of a section of pipe models a longitudinal crack 28 in the pipe. An end section 30 of pipe, shows the crack depth 31 and the bottom of the crack, as well as the associated elevated stress on the pipe at the bottom. The modeled crack 28 has a width that varies with the pressure in the pipe. The crack also has a depth 31 and a staring point 32, which is the crack tip.

Based on Elastic Plastic Fracture Mechanics together with consideration for plastic collapse theory, the failure pressure is determined for a critical crack flaw size characterized by an axial length and wall depth of the crack. A comparison is drawn between critical flaw sizes when the pipeline is operated at normal operating pressure versus the critical flow sizes predicted if the pipeline were to be subjected to higher pressure as is the case with a hydrostatic test. In using the critical flaw size prediction at hydrostatic test as an acceptable flaw size limit for in-line inspection, a flaw growth rate is applied to the largest defect left in the pipeline and the safe re-inspection, interval can be established for the pipeline. Tests other than hydrostatic tests may be applied to determine the acceptable flaw size limit.

Using the finite element analysis of the pipe and considering incremental plasticity of cracks in the pipe, the width of the crack can be modeled for different pressures in the pipe. By running the finite element analysis of a type of pipe at various pressures, a curve 34 (FIG. 4) is developed of the width of a stress crack (CMOD) at various internal pipe pressures. A curve 34 is generated for each type of pipe, where for example, a pipe type is defined by the pipe diameter and length. A threshold level 38 is established for a minimum crack width (CMOD). In the example shown in FIG. 4, the threshold CMOD is 0.004 inch.

Figure 4:
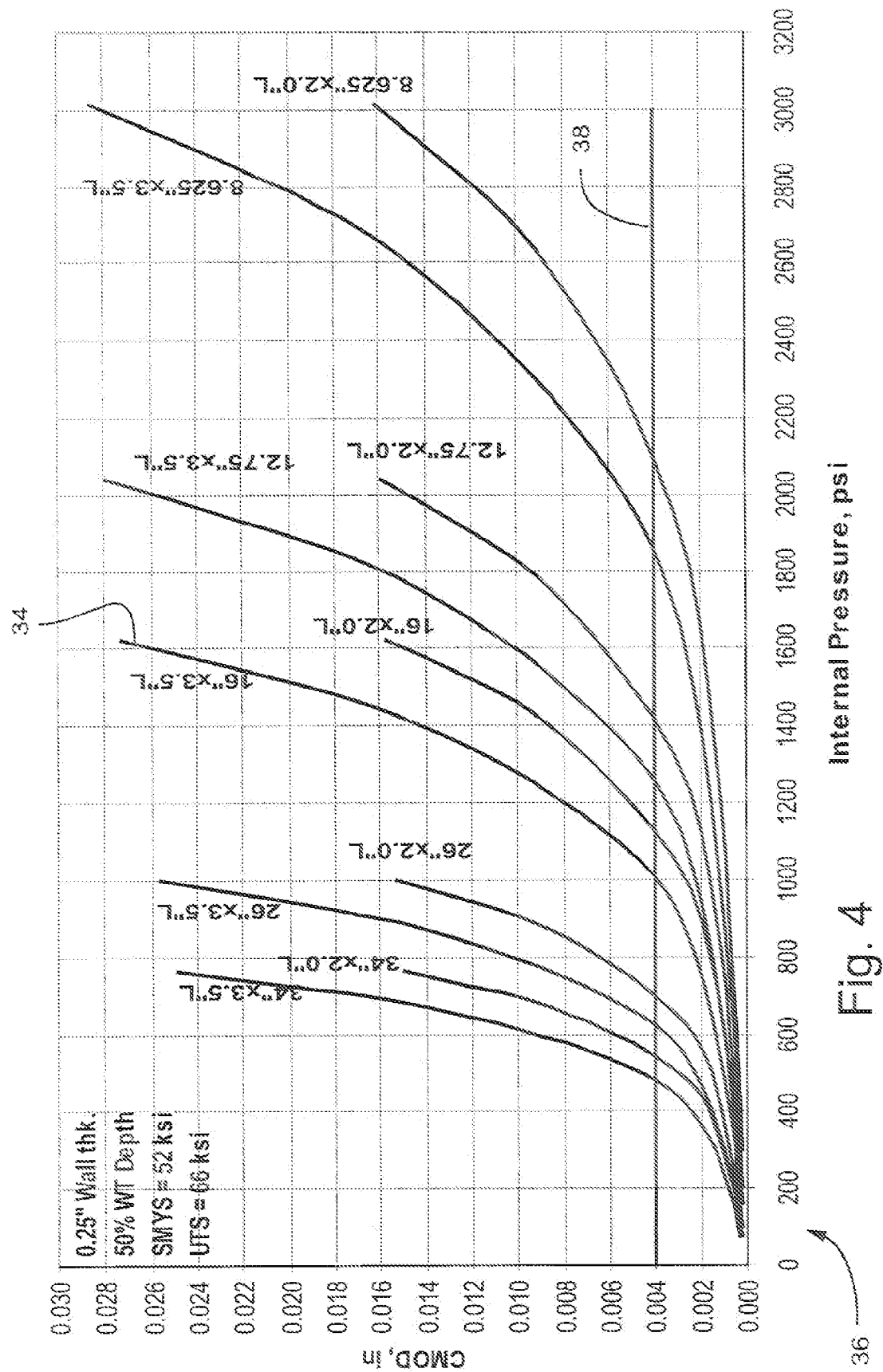
FIG. 4 is a chart of pipe types correlating internal pipe pressure to crack width (CMOD).

FIG. 4 shows the minimum internal pipe pressure needed for the threshold CMOD 38 for several pipe diameters and pipe section lengths. FIG. 4 is a chart 36 of a family of curves 34 describing the mechanical shape behavior of cracks for a series of pipelines with common wall thickness and material grade. An element of the preassessment process 22 is to determine the operating pressure necessary during the conduct of the inspection in order to insure for a given pipeline the crack opening is at least 0.004 inch which is the minimum required for detection based on application of the TFI magnetic flux leakage data tool. The chart 36 is of internal pipe pressure (psi—pounds per square inch) versus CMOD (inches). The chart is applicable to a specific type of pipe, e.g., having a 0.25 inch wall thickness, 50% WT dept, SMYS is 52 ksi, at UTS is 66 ksi. The chart has a series of curves each applicable to a certain section of pipe having a particular diameter and length. The curves identify the internal pipe pressure needed to have a certain CMOD level.

The MFL-TFI flux data screening process may have a minimum CMOD level 38. The chart 36 aids in determining the internal pipe pressure needed to achieve the minimum CMOD 38 for a particular pipe type, diameter and section length. The determination of internal pipe pressure needed to achieve a CMOD level is conducted in the preassessment phase 22.

If the preassessment 22 determines that the pipe and its internal pressure is at or above the threshold 38, a conventional magnetic flux sensor probe 13 unit is applied to the pipe to collect magnetic flux data. The sensor unit collects magnetic flux data, including a MFL data (step 40) and TFI data (step 42). A conventional high resolution inline magnetic flux inspection tool may be used to collect magnetic flux data in steps 40 and 42.

The MFL and TFI flux data are processed in a conventional manner in step 44. The processed data are displayed as images on a computer display screen and aligned such that they can be compared side-by-side on the screen or other computer output devices, e.g., paper printer. For example, the images of MFL flux data from a section of pipe are displayed next to TFI data images representing the same section of pipe. The pipeline management system includes software that displays the visual images of the MFL and TFI data such that the side-by-side displayed visual MFL and TFI data images are of the same section of the pipeline. For example, the software may have a playback mode that allows a technician to view the MFL and TFI data images stored in the data storage device 18, and scroll the data images to allow the technician to inspect a section of the pipe.

Criteria can be applied to evaluate the TFI data and MFL data. The application of the criteria, step 68 in FIG. 2, may be used to determine whether the SCC cracking is sufficient to necessitate inspection and maintenance of a section of pipe. The criteria may vary depending on the application of the TFI-MFL, data inspection process, the sizes and types of pipes evaluated, the history of prior pipe inspections, and other factors. An example of a criteria is (Criteria 1 or C1) includes an analysis for determining possible crack fields (PCFs). A second exemplary criteria (Criteria 2 or C2) includes an analysis for a threshold of metal loss (e.g., 30%) in the pipeline.

Figure 5:
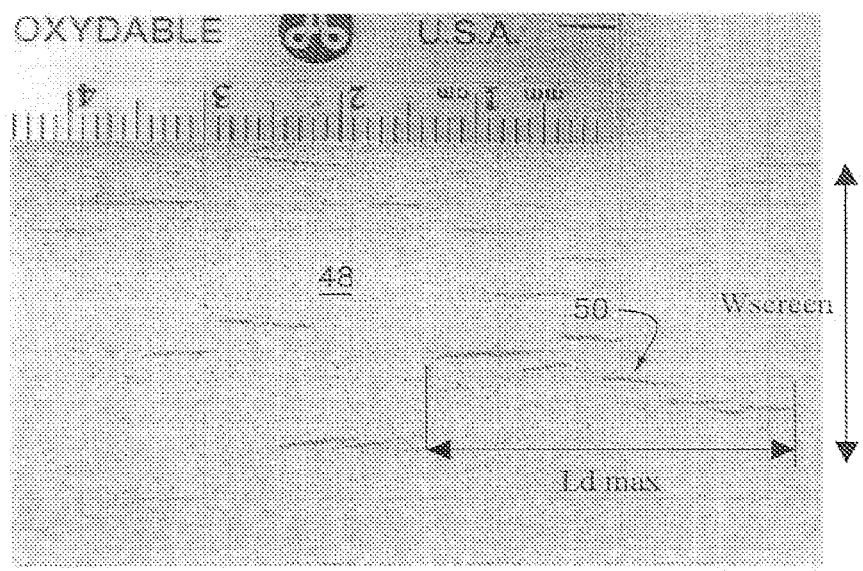
FIG. 5 is a photograph of a pipe section having SCC.
Figure 6:
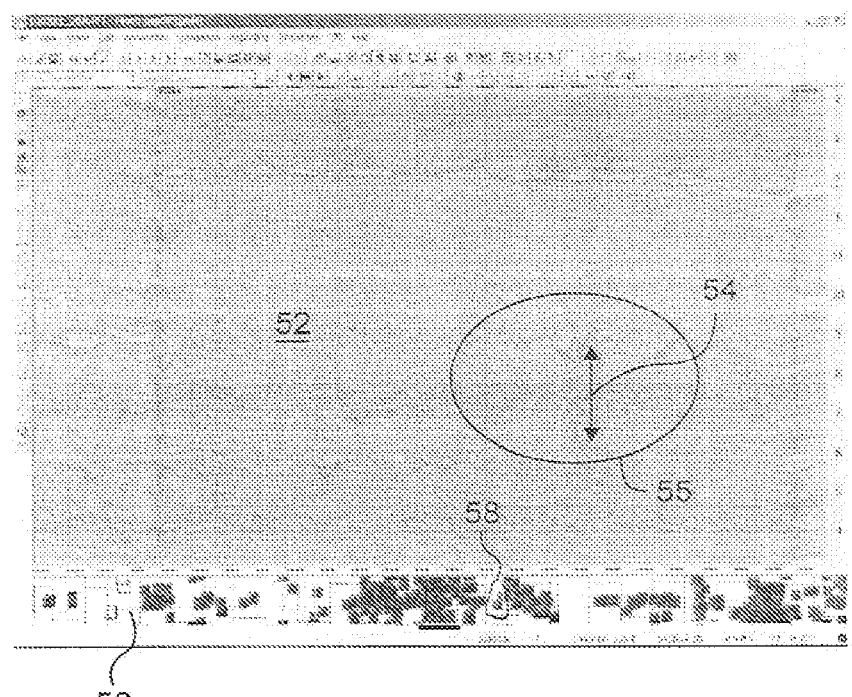
FIG. 6 is an exemplary computer screen image of TFI data of a section of a pipe.
Figure 7:
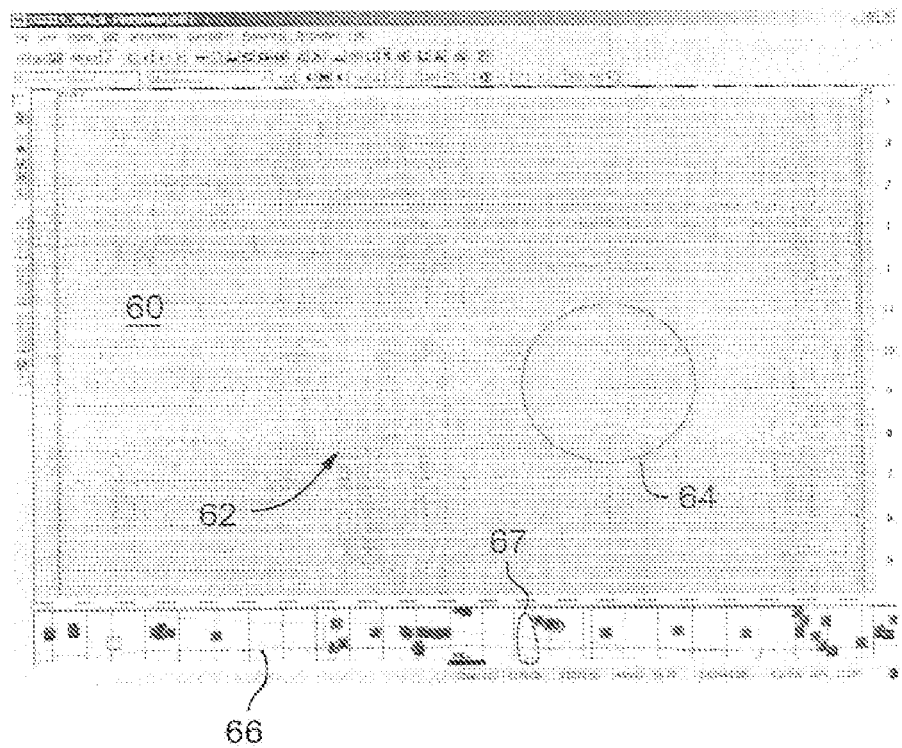
FIG. 7 is an exemplary computer screen image of a MFL data of a section of a pipe.

The analysis of possible crack fields for Criteria 1 is illustrated in FIGS. 5, 6 and 7. FIG. 5 is a photograph 48 of a section of pipe having stress corrosion cracking (SCC) cracking 50. A ruler in the photograph shows the scale of the cracking. The dimensions "Wscreen" and "Ld max" illustrate the dimensions of one or both of the fields of view of the MLF and TFI data images displayed in FIGS. 6 and 7. As magnetic flux detection probe(s) pass through the pipe, they generate signals representative of the magnetic flux disturbances caused by the flaws in the pipe. These signals provide information regarding SCC in the pipe. The MFL and TFI data images may be stored and/or displayed, in real time or at a later time in a play back mode. FIG. 6 is an exemplary image 52 of a TFI data image of the section of pipe. FIG. 7 is an exemplary image of a MFL data image of the same section of pipe represented in FIG. 6. The TFI data image 52 and MFL data image 60 are displayed simultaneously, e.g., side-by-side, on a computer screen. The simultaneous display allows the user to inspect simultaneously the MFL and TFI data for the same section of the pipe. The display of MFL and TFI data can be scrolled to show successive sections of the pipe. By scrolling the MFL and TFI data images, a user may remotely inspect a pipe.

The TFI data image 52 corresponds to a small section of pipe, such of an area the size of Wscreen and Ld max shown in FIG. 5. The TFI data image shows changes 54 in the TFI at various regions of the pipe section. The data changes 54 indicate a variation in the traverse magnetic flux which may indicate a potential SCC cracking in the pipe. The narrow screen image 56 along a row at the bottom of the TFI data display image 52 is a map of the a larger pipe section, e.g., 100 feet of pipe, and shows the location 58 of the TFI data image 52 and identifies locations (see black spots) of significant TFI data variations. A technician may move the MFL and TFI screen data to the areas corresponding to the black spots to determine whether excessive SCC cracking is indicated.

The MFL data image 60 (FIG. 7) shows a image of magnetic flux data. Disruptions in the data, e.g., 62, indicate potential SCC cracking. A pipe map 66 along the bottom of the signal image 60 indicates the location 67 of the image 60 and other potential significant cracks in the pipe.

The circle 55 (FIG. 6) in the TFI data image refers to the same section of pipe that corresponds to the circle 64 (FIG. 7) in the MFL data image. It should be noted that substantially no flux signal changes are shown in MFL circle 64 while there are significant signal variations in the TFI data image shown in circle 55. The side-by-side display of MFL and TFI data images assist users in detecting cracks that may not be apparent with only one of MFL or TFI data available for inspection.

In the example shown in FIGS. 6 and 7, the TFI and MFL data are displayed as generally parallel lines of data aligned longitudinally with the pipe axis. The lines roughly correspond to the inner surface of the pipe. The lines represent the magnetic flux levels along a line extending generally longitudinal along the pipe. Each line corresponds to a "channel" of flux data. Viewing several adjacent channel lines of flux data provides an indication of the flux on the inner surface of the pipe. A variation in the flux is indicated by a disruption, e.g., variation in shading or wiggle, in one or more of the flux channel lines.

The process of data comparison determines the existence of a probable crack field is based on the two types of magnetic flux leakage data inspection (MFL and TFI) that are used to observe occurrences of high pH stress corrosion cracking and behavior morphology predicted by the accepted theory of high pH SCC initiation. The theory and observed SCC behavior indicates that areas of low corrosion indicated by the MFI magnetic flux leakage inspection accompanied by any magnetic flux anomaly indicted by the TFI inspection tool would have a high probability of a crack field existing in the pipeline thus the determination of a PCF. A specific set of criteria (C1) is applied to analyzer the respective signal data to insure detection while minimizing the possibility of a false positive report of a PCF. If the criteria is not met by the signal data, it is determined that there is a low likelihood that a PCF is present.

To apply Criteria 1 (C1), a designated threshold is established for analyzing the TFI signal image. The identified TFI signals that satisfy the criteria, are further evaluated, with another sub-criteria, to determine whether a signal feature or crack meets a PCF pattern potential (e.g., signal amplitude that occurs in 10 or fewer channels). The TFI signal threshold is applied automatically by the computer program and is variable depending upon characteristics of pipeline being evaluated. The pipeline may be evaluated by applying a series of thresholds.

If it is determined that the TFI signal feature or crack has an amplitude greater than the threshold and the PCF pattern potential meets the sub-criteria, the MFL data relating to the same location or signal feature is compared to the corresponding TFI data. If there exists a signal on the TFI and a lack of a significant MFL signal (e.g., less than 2% signal variation), the existence of a reportable PCF is inferred. The presence of a reportable PCF may indicate that the corresponding section of pipe should be inspected, evaluated and possibly repaired or replaced.

Once criteria 1 (C1) (MFL variation less than 2% and TFI variation is greater than the signal amplitude and less than 10 channels) has been completed for one section of pipe, the MFL and TFI data images are moved to another section of pipe and criteria one is applied to that section. The application of criteria one and criteria two is repeated for each section of pipe shown in the comparative images of MFL and TFI data.

Figure 8:
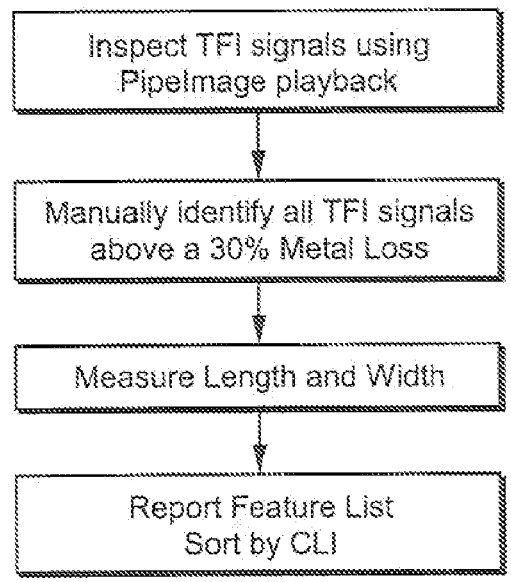
FIG. 8 is a flow chart for a second criteria analysis (C2) applicable to detect likely locations for a second type crack (non-classic SCC) initiated by a second mechanism that occurs near neutral pH SCC.

FIG. 8 is a flow chart for a second criteria analysis (C2) applicable to detect likely locations for a second type crack (non-classic SCC) initiated by a second mechanism that occurs near neutral pH SCC. The second type of crack is generally associated with metal loss or significant aligned surface corrosion. A signal image of the pipe is displayed in a scrolling manner to allow a technician to inspect the pipe remotely. The analysis (C2) for the second type of crack is preformed by searching for TFI signals above a specified metal loss threshold (e.g., 30%). These cracks may be identified manually by visual inspection of the TFI data image.

The length and the width of the TFI data image is measured. The results of the length and width measurement of TFI data are used to generate a corrosion linearity index (CLI) for the TFI data disturbance. The CLI may be determined by dividing the length of the crack signal image by the width of the TFI data image. A short wide TFI signal image may have a CLI equal to one. A long thin TFI signal image may have a CLI equal to 2.5 or greater. TFI signal images having a CLI greater than a threshold level, e.g., substantially 2.5 or 5.0, are high probability locations for near neutral ph SCC. A CLI threshold is established at, for example, 5.0. Features with a corrosion linearity index greater than 5 are reported for further processing.

At step 82 (FIG. 2 and FIG. 9), a discovery prioritization list is generated for the SCC crack sites that were identified using criteria C1 and C2. The list is generated and processed using the results of analyses performed for criterias 1 and 2 (i.e., PCF feature list and CLI feature list, respectively). If the features (PCF/CLI) number less than 25, all pipeline feature locations are excavated to provide direct examination of each potential SCC location. Setting the threshold at 25 or some other number of PCF/CLI features may be made based on the costs of excavating locations of predicted SCC features or other factors. If there are more than a threshold number of identified PCF/CLI features, e.g., 25 features, on the priority list, then a select number, e.g., twenty (20), PCF/CLI features are selected for excavation.

If the excavations reveal that SCC is present, step 84, then all pipeline sites corresponding to the PCF/CLI features may be excavated in step 86. Alternatively, other conventional pipeline inspection techniques can be employed, step 24. For example, a full-length hydrostatic or CD slug test can be performed on the pipeline at step 24 to fully assess the defects. The results of the full-length testing are also stored in the storage device 24. Similarly, if the cracks in the excavated pipe locations are greater than a critical size, step 88, other conventional pipeline inspection techniques may be used to inspect the pipeline. A critical size may be defined using the susceptibility data and historical data described above. In an exemplary embodiment, the critical size is defined by, and is further dependent upon, the probable risks associated with the defect in terms of the consequences of not taking further action.

If cracks less than a critical size (step 88) are found during the excavations, a re-inspection plan (step 90) is devised for the SCC feature(s) in accordance with any limits of detection and the results (and reinspection plan) are stored in the storage device 18 at step 92. If the defects do not exceed a defined critical size, then hydrostatic or CD slug testing (step 90) is performed on a portion of the pipeline and the results are stored in storage device 18. Further, the criteria (C1 and C2) may be adjusted, e.g., CLI threshold raised, if the excavation reveals a lack of critical size crack defects.

If no crack features are identified based on the excavations (step 84), a conclusion is reached of no SCC (step 94) threat and that the pipeline cracks are survivable for 5 years (step 96). These conclusions are stored in computer memory for later use, such as for comparison with crack data obtained from inspection of excavated pipeline sections.

Figure 9:
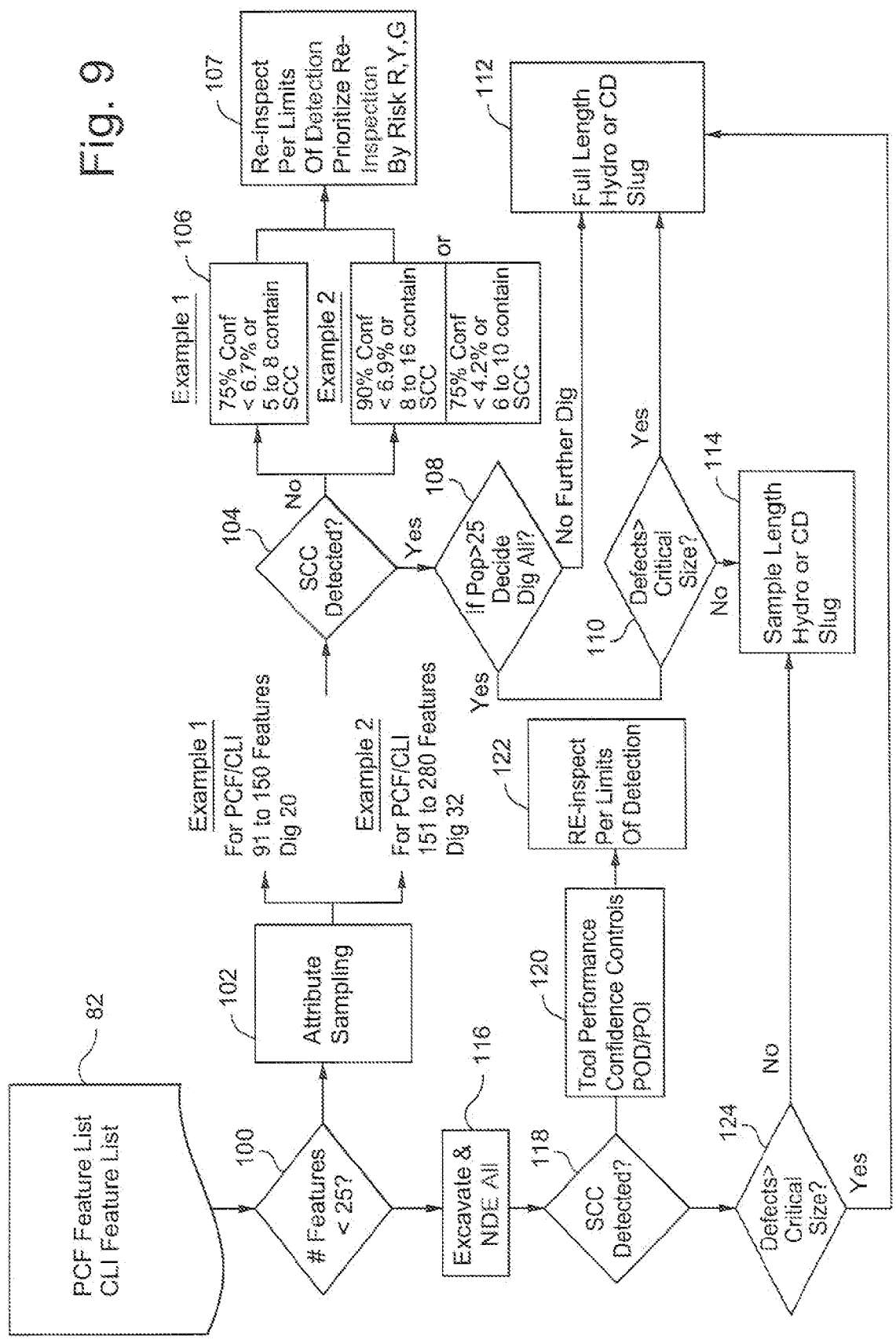
FIG. 9 is a flow chart for discovery excavations for validating the MFL and TFI detection of SCC.

A more detailed description of the discovery excavation process follows with reference to FIG. 9. If (step 100) there are more than a threshold, e.g., 25, number of SCC features listed in the discovery prioritization list 82, attribute sampling, e.g., excavate twenty SCC feature sites if there are 91 to 150 features (Step 102, Example 1) and excavate thirty-two SCC features if there are more than 150 features (Step 102, Example 2), is performed to select a sub-group of the pipe crack features to be excavated, in step 102. Attribute sampling identifies the SCC features to be physically observed by excavating the pipeline at the SCC feature sites. A positive result for SCC is the physical observation of cracks in the pipeline during a direct examination or excavation. A negative result is a direct examination of the pipeline surface at a location predicted by the screening process with no indication of cracking detected by direct examination. In step 104, if SCC is detected during the attribute sampling and associated physical inspections, a determination is made as to whether to excavate any remaining SCC features in step 108. If no SCC features are detected the crack detection from physical inspection, a re-inspection plan (step 107) is devised in accordance with the limits of detection and the results of the sampling (as well as the reinspection plan) are stored in the storage device. For example, if no SCC cracks are detected by physical inspection, then there may be 75% confidence that less than 6.7% of the pipeline has SCC cracking (i.e., 5 to 8 SCC features in the pipeline, Step 106, Example 1) and 90% confidence that less than 6.9% of the pipeline has SCC features (i.e., 8 to 16 features in a pipeline length, Step 106, Example 2). Based on the confidence determination, a re-inspection plan is devised for a future TFI-MFL inspection in step 107.

If all of the SCC sites are excavated and physically inspected (steps 116, 118) but no SCC cracks are evident from the physical inspection, the thresholds are adjusted in the criteria (C1 and C2) used to screen the TFI and MFL data in step 120. For example, the signal threshold for a variation in the TFI signal (see criteria 1) may be increased. Subsequent remote inspections are performed using the criteria with the adjusted thresholds.

If SCC has been detected at step 104, it is determined whether all of the locations listed in the prioritization list 82 should be excavated in step 108. This may be a decision made based upon a cost-benefit evaluation (i.e., the costs of performing a number of excavations versus the potential risk of not performing the excavation). If it is determined that it is not necessary or economically feasible to excavate on all locations, a full length conventional test, e.g., hydrostatic or CD slug test, of the pipeline may be performed in step 112 and the results stored in the electronic storage device. Alternatively, if it is economically feasible to excavate all identified SCC sites on the priority list (steps 108, 116), a determination is made from the physically inspection of the excavated sites as to whether any of the SCC cracks exceed a critical size in steps 110 and 124. If SCC cracks exceed a critical size, a full length hydrostatic or CD slug test is performed on the selected locations at step 112. Otherwise, a sample length hydrostatic or CD slug test is performed at step 114 and the results are stored in storage device.

As indicated above, the results of the processes described above with respect to the flow diagram of FIG. 2, are stored in the storage device. Various reports may be generated from these results for use in predicting the risks of SCC in pipelines. A sample report is shown in FIG. 8. Utilizing the information obtained from the implementation of the pipeline management application, in conjunction with the historical inspection files, pipeline specifications, and other data, SCC risks may be predicted with greater accuracy. The sample report 130 of FIG. 10 provides a side-by-side comparison of the originally-predicted risks associated with a pipeline that were generated using traditional SCC processes (column 132) and the predicted risks resulting from the implementation of the pipeline management system processes (column 134). Also shown in the report 130 are anomalies 136 determined as a result of the execution of the pipeline management system processes which provide insight into the nature of the results of inspections and evaluations of the inspection data.

As indicated above, the pipeline management system provides a pipeline solution for screening pipelines for SCC. The pipeline management system functions may be applied to both longitudinal as well as circumferential cracking. Pipelines services may be liquid or gas pipelines. The pipeline management system processes assesses the factors of stress intensification at crack tips using fracture mechanics and the effects on flux leakage. Using this and other information, the pipeline management system process includes performing one or two inspection runs on a pipeline to collect MFL and TFI data, aligning and evaluating the collected MFL and TFI data, and developing an action plan for the pipeline that includes reinspections, direct examinations, hydrostatic or CD slug testing, and other activities. The results of the analysis may be used to determine the risk of SCC.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for detecting stress corrosion cracking (SCC) of pipelines, comprising:
   identifying pipeline locations and pipeline conditions that are amenable to inspection by a magnetic flux tool;
   performing two inspections on the pipeline, one inspection is performed to collect the magnetic flux inline (MFL) data and a separate inspection is performed to collect transverse magnetization flux lines (TFI) data, wherein the MFL data and TFI data are distinct;
   after collection of the TFI data and the MFL data, aligning separate signals descriptive of pipeline features generated from each of the MFL data and the TFI data, wherein the alignment includes presenting the separate signals simultaneously to show the same pipeline feature;
   evaluating a number of pipeline features indicated by the aligned separate signals from the MFL data and TFI data, the features including potential crack field features and potential corrosion features, and
   based upon results of the evaluation identifying potential crack fields for physical inspection.

2. The method of claim 1 wherein identifying potential crack fields for physical inspection includes performing at least one of:
   excavating and inspecting all locations associated with the features, and
   excavating and inspecting a selected number of locations associated with the features.

3. The method of claim 1 wherein the identifying pipeline locations and pipeline conditions includes determining whether a pressure in the pipeline is sufficient to perform the inspections.

4. The method of claim 1 wherein the potential crack field features are determined by a process comprising:
   identifying TFI data variations occurring above a specified threshold;
   identifying MFL data for a section of pipeline corresponding to the identified TFI data;
   for the identified TFI data, determining whether MFL data variations are below a second threshold level;
   designating the sections of the pipeline corresponding to identified the TFI data above the threshold and below the second threshold as a potential corrosion feature.

5. The method of claim 1 wherein the potential corrosion features are determined by a process comprising:
   identifying TFI signals that indicate a section of the pipeline exceeding a defined metal loss percentage;
   measuring a width and length of the signal features, and if the width and length of the signal feature exceed threshold crack width and length values, designating as a potential corrosion feature section of pipeline corresponding to the identified TFI signals.

6. The method of claim 1 wherein the potential crack field features are determined by a process comprising:
   identifying TFI signals occurring above a specified threshold;
   identifying MFL signals for a section of pipeline corresponding to the identified TFI signals;
   for the identified TFI signals, determining whether the MFL signals are below a second threshold level;
   designating the sections of the pipeline corresponding to identified TFI signals above the threshold and below the second threshold as a potential corrosion feature;
   identifying TFI signals that exceed a defined metal loss percentage;
   measuring a width and length of the signal features, and if the width and length of the signal feature exceed threshold crack width and length values, designating as a potential corrosion feature section of pipeline corresponding to the identified TFI signals.

7. The method of claim 1 wherein the designated sections of the pipeline corresponding to identified TFI signals above the threshold and below the second threshold as a potential corrosion feature are listed in a priority list and the list is used to determine which crack fields to be physically evaluated.

8. The method of claim 1 wherein the physical evaluation comprises excavating the pipeline in an area identified as potential corrosion feature.

9. The method of claim 1 wherein the two inspections are performed simultaneously.

10. The method of claim 1 wherein the two inspections are performed sequentially.

11. A method for detecting stress corrosion cracking (SCC) of pipelines, comprising:
    identifying pipeline locations and pipeline conditions that are amenable to inspection by a magnetic flux inline tool and by a TFI tool;
    performing two inspections on the pipeline, one inspection performed using the magnetic flux inline (MFL) tool and an other inspection performed using the TFI tool;
    aligning signal features resulting from the two inspections;
    identifying TFI signals occurring above a specified threshold;
    identifying MFL signals for a section of pipeline corresponding to the identified TFI signals;
    for the identified TFI signals, determining whether the MFL signals are below a second threshold level;
    designating the sections of the pipeline corresponding to identified TFI signals above the threshold and below the second threshold as a potential corrosion feature;
    identifying TFI signals that exceed a defined metal loss percentage;
    measuring a width and length of the signal features, and if the width and length of the signal feature exceed threshold crack width and length values, designating as a potential corrosion feature section of pipeline corresponding to the identified TFI signals.

12. The method of claim 11 wherein identifying potential crack fields for physical inspection includes performing at least one of:
excavating and inspecting all locations associated with the features, and
excavating and inspecting a selected number of locations associated with the features.

13. The method of claim 11 wherein the identifying pipeline locations and pipeline conditions includes determining whether a pressure in the pipeline is sufficient to perform the inspections.

14. The method of claim 11 wherein the physical evaluation comprises excavating the pipeline in an area identified as potential corrosion feature.

15. The method of claim 11 wherein the two inspections are performed simultaneously.

16. The method of claim 11 wherein the two inspections are performed sequentially.

17. A computer program product stored on a computer readable medium for detecting stress corrosion cracking (SCC) of pipelines, the computer program product including instructions for performing:
identifying pipeline locations and pipeline conditions that are amenable to inspection by a magnetic flux inline tool and by a transverse magnetization flux lines (TFI) tool;
performing two separate inspections on the pipeline, one inspection performed using the magnetic flux inline tool and an other inspection performed using the TFI tool;
aligning signal features resulting from the two inspections, wherein the alignment includes presenting simultaneously the signal features from the two inspections that show the same features of the pipeline;
evaluating the aligned signal features, wherein the evaluation comprises:
using the aligned signal features to identify pipeline features detected by the two inspections, the features including potential crack field features and potential corrosion features; and
based upon results of the evaluating, performing at least one of: excavating and inspecting all identified pipeline features and excavating and inspecting a selected group of the identified pipeline features.

18. The computer program product of claim 17, wherein the identifying pipeline locations and pipeline conditions includes:
gathering pipeline information including:
past inspection results;
pipeline operating conditions; and
pipeline specifications; and
based upon the evaluating, determining whether a specified inspection tool is capable of returning accurate inspection data relating to the condition of the pipeline.

19. The computer program product of claim 17, wherein the past inspection results includes:
number of defects in the pipeline;
size of the defects in the pipeline;
extent of the defects in the pipeline; and
a critical size determined for each of the defects.

20. The computer program product of claim 17, wherein the potential crack field features are determined by:
identifying TFI signals occurring above a specified threshold;
for TFI signals occurring above the specified threshold, identifying any potential crack field patterns;
for TFI signals that are identified with a pattern, analyzing magnetic flux inline (MFL) data that are aligned with TFI signals identified with the pattern;
determining a likelihood of presence of stress corrosion cracking for features associated with the pattern where results of the analyzing magnetic flux inline data indicate a lack of signal and where a TFI signal is present.

* * * * *